United States Patent [19]

Floeder et al.

[11] Patent Number: 5,403,722
[45] Date of Patent: Apr. 4, 1995

[54] TECHNIQUE TO COUNT OBJECTS IN A SCANNED IMAGE

[75] Inventors: Steven P. Floeder, Arden Hills, Minn.; Josef A. Graessle, Northine-Westphalia, Germany; John C. Schultz, Afton, Minn.; Werner R. Schwarz, Northine-Westphalia, Germany; Frederick M. Waltz, Mendota Heights, Minn.

[73] Assignee: Minnesota Mining and Manufacturing Company, Saint Paul, Minn.

[21] Appl. No.: 272,996

[22] Filed: Jul. 14, 1994

Related U.S. Application Data

[63] Continuation of Ser. No. 912,887, Jul. 13, 1992, abandoned.

[51] Int. Cl.⁶ .............................................. C12Q 1/00
[52] U.S. Cl. .................................... 435/39; 435/40; 435/291
[58] Field of Search ............................ 435/39, 40, 291

[56] References Cited

U.S. PATENT DOCUMENTS

| | | | |
|---|---|---|---|
| 3,493,772 | 2/1970 | Daughters, II et al. | |
| 3,736,432 | 5/1973 | Sweet | 250/222 PC |
| 3,764,480 | 10/1973 | Sedlicka et al. | 435/40 |
| 3,811,036 | 5/1974 | Perry | 235/92 PC |
| 3,972,778 | 8/1976 | Cunningham | 435/291 |
| 4,116,775 | 9/1978 | Charles et al. | 435/291 X |
| 4,118,280 | 10/1978 | Charles et al. | 435/291 |
| 4,456,380 | 6/1984 | Kondo et al. | 356/418 |
| 4,535,239 | 8/1985 | Brighton | 250/339 |
| 4,554,867 | 11/1985 | Thumm | 100/3 |
| 4,565,783 | 1/1986 | Hansen et al. | 435/299 |
| 4,637,053 | 1/1987 | Schalkowsky | 435/291 X |
| 4,896,966 | 1/1990 | Boisseau et al. | 435/291 X |
| 5,111,809 | 5/1992 | Gamble et al. | 128/204.18 |
| 5,117,467 | 5/1992 | Misaki et al. | 382/6 |

FOREIGN PATENT DOCUMENTS

| | | |
|---|---|---|
| 0301600 | 7/1987 | European Pat. Off. |
| 2602074 | 1/1988 | France |
| 2443410 | 10/1981 | Germany |
| 59-187777 | 10/1984 | Japan |
| 2-6729 | 2/1990 | Japan |
| 2227346 | 7/1990 | United Kingdom .......... G06K 9/62 |
| 1434465 | 1/1987 | U.S.S.R. |

OTHER PUBLICATIONS

"Count Up to 1000 Objects in a Field, Automatically", by Artek Systems Corporation (3 pages). Jul. 1973.
"Electronic Colony Counters", by VSMF (3 pages). Jul. 1973.

*Primary Examiner*—Robert J. Warden
*Assistant Examiner*—Krisanne M. Thornton
*Attorney, Agent, or Firm*—Gary L. Griswold; Walter N. Kirn; Paul W. Busse

[57] ABSTRACT

The present invention relates to a method and apparatus for counting the number of microorganism colonies present on a disposable microorganism culturing device having a substantially planar substrate. The preferred apparatus of the present invention includes an LED bar illuminating the surface of the substrate and a linear array of SELFOC lenses which focus the light reflected off of the substrate onto a linear CCD sensor array. The CCD sensor array is connected to a microprocessor which analyzes the raster-scanned data using the preferred algorithm. The preferred algorithm uses the sigma-shaped neighborhood for image processing. The preferred algorithm passes the sigma region across the image in a raster-scanned order to detect object starts and merges which yield a colony count for a scanned microorganism culturing device.

9 Claims, 5 Drawing Sheets

5,403,722

TECHNIQUE TO COUNT OBJECTS IN A SCANNED IMAGE

This is a continuation of application Ser. No. 07/912,887, filed Jul. 13, 1992, now abandoned.

FIELD OF THE INVENTION

This invention relates to a method and apparatus for counting the number of distinct objects in a scanned image. In particular, it relates to a method and apparatus for counting the number of microorganism colonies present on a substantially planar substrate.

BACKGROUND OF THE INVENTION

Different methods and devices are known for counting microorganism colonies in, for example, petri dishes. Manual counting of colonies by trained laboratory personnel is well-known. This method has many disadvantages. They include the costs associated with the use of skilled technicians to perform the time-consuming chore of manual counting as well as the limited accuracy in the counts achieved.

Automated counting systems are also known. They can be separated into two basic categories. The first category includes those systems employing cameras or video equipment in conjunction with hard-wired circuits or digital computers to count the number of colonies in a petri dish. Examples of such systems are described in EP Publication No. 0 301 600; U.S. Pat. No. 3,811,036 to Perry; and French Publication No. 2 602 074.

Video-based systems suffer from a number of disadvantages. The primary disadvantage is the expensive and sophisticated equipment used in such systems to process the raw pixel image produced by the video cameras. To avoid multiple counting of the same colonies such systems typically include processing-intensive labelling schemes requiring relatively powerful computer systems to accurately count of the number of colonies in an acceptable amount of time.

An additional disadvantage is that many of these video-based systems require that the petri dishes be illuminated through their bottom surface which requires a substrate which is light permeable to ensure accurate counting. The illumination is typically required because of the thickness of the agar used in petri dishes results in colonies growing on the surface of the agar as well as in the middle and on the bottom of the agar. Surface illumination only would result in undercounting of the colonies in the middle and on the bottom of the agar. In other systems, such as that described in EP 0 301 600, the absorbance and transmission of light is used to detect colonies.

The growth of colonies throughout the vertical thickness of the medium is not a particular problem for lasers of the disposable microorganism culturing devices such as PETRIFILM TM, manufactured by 3M Company. Such devices have a very thin layer of growth medium making all colonies visible with surface illumination. The substrate is not, however, sufficiently permeable to light for use with many of the known automated counting systems.

In addition to the cost and complexity of the hardware configurations of known automated video counting systems, the object counting algorithms used with systems employing digitization of the images also suffer from disadvantages.

A simple Euler number can be used to identify objects in a raster-scanned image and can be used with only a single pass through the image, but detects only 4-connected objects. This can give spurious results when 8-connected images are present in the scanned image.

At the opposite extreme, a full-connected component analysis detects all objects, whether they are 4-connected or 8-connected. That type of analysis, however, involves complicated-labeling and tagging operations which can require multiple passes through the image, as well as significantly more complex and costly hardware.

The second category of automated counting systems typically uses an array of photodetectors and hard-wired circuitry to perform the counting process. As with most of the video-based systems, the counting systems using photodetectors are also limited by the requirement that the petri dish be illuminated through its substrate to produce an accurate count. As a result, the substrate on which the colonies are contained must be light permeable, which is a particular problem with disposable culturing devices such as PETRIFILM TM.

Examples of such systems are disclosed in U.S. Pat. No. 3,493,772 to Daughters II et al. as well as U.S. Pat. No. 3,736,432 to Sweet. The Daughters' device includes a light source located below the petri dish and uses the colonies as lenses to focus the light on a linear array of photodetectors. The Sweet device employs a light source below the petri dish which uses the light absorbency of the bacterial colonies to produce dark spots on a linear photo detector. Both systems use dedicated circuitry to perform the counting process.

The Daughters and Sweet devices both use a linear array of photodetectors and rely on voltage changes to inhibit counting by neighboring photodetectors, thereby avoiding multiple counting of individual colonies. That circuitry can cause errors in counting because colonies which may or may not be opaque or light permeable may not be counted with a given system. Other errors can occur in the counting of tree-shaped or other complex shaped colonies.

SUMMARY OF THE INVENTION

The present invention provides significant advantages over known automated counting systems. Primary among those advantages is that the preferred apparatus is developed specifically for use with disposable devices for culturing microorganisms as described in U.S. Pat. No. 4,565,783 to Hansen et al., which is hereby incorporated by reference.

Commercial embodiments of the devices described in Hansen are marketed under the tradename PETRIFILM TM by 3M Company. Many PETRIFILM TM products include substrates which are not substantially light permeable and, therefore, render many of the previously known devices for counting colonies in standard petri dishes unusable. In addition, many of those systems are adapted for use with standard petri dishes having a deep well to hold the culturing medium, not the substantially planar PETRIFILM TM products.

The present invention eliminates the disadvantages of the known systems as described above. In particular, the present invention does not require illumination through the substrate and is adapted for use with microorganism culturing devices having a substantially planar substrate, such as PETRIFILM TM. The present invention also provides a fast and accurate count of colonies using readily available linear arrays of light sources, lenses and image sensors—many of which were developed for use in facsimile or photocopying machines. These components are connected to readily available microprocessors and use the algorithm described below to accurately and quickly perform the counting process without labelling or long-term storage of the data to avoid multiple counting of individual colonies.

In its simplest form, the preferred apparatus of the present invention includes a LED bar illuminating the surface of the substrate and a linear array of SELFOC lenses which focus the light reflected off of the substrate onto a linear CCD sensor array. The CCD sensor array is connected to a microprocessor which analyzes the raster-scanned data using the preferred algorithm.

In the preferred embodiment, the apparatus is electrically connected to a remote computer for automatic data transfer and storage.

The preferred image processing system includes an automatic calibration feature which calibrates the sensors by scanning a blank substrate to determine a threshold level above which objects will be counted.

Also contemplated for use in the present invention is a cassette mechanism to automatically feed a number of substrates through the scanning apparatus in a manner similar to the automatic feeding of paper through a photocopying machine.

Barcode labels can also be incorporated into the culturing devices to simplify the transfer of information from the preferred apparatus to other electronic equipment. In the preferred apparatus, the LED array and CCD sensors used to detect colonies are also used to read the barcode labels.

The preferred algorithm developed for use with the present invention also offers advantages not available with known object counting algorithms. Like an Euler number analysis, the preferred algorithm can be used with only a single pass through the image. Its advantage over the Euler number analysis is that the preferred algorithm can detect 8-connected objects in addition to the 4-connected images to which a Euler number analysis is limited. The preferred algorithm does so without requiring multiple passes through the image or the complexity and cost associated with a full-connected component analysis algorithm including labeling of the pixels from the entire image.

In addition, the preferred algorithm is particularly useful for inspection tasks requiring relatively high image processing speeds because its use of raster-scanned data and limited processing neighborhood are tailored for high speed data processing using relatively simple hardware. In contrast, the known systems described above require complex hardware configurations to implement complex data analysis schemes. As a result, they typically cost $10,000 or more.

These and various other advantages and features which characterize the present invention are pointed out witch particularity in the claims annexed hereto and which form a part hereof. However, for a better understanding of the invention, its advantages, and the objects obtained by its use, reference should be made to the .drawings which form a further part hereof, and to the accompanying descriptive matter, in which there are illustrated and described preferred embodiments of the invention.

DESCRIPTION OF THE PREFERRED EMBODIMENTS

Figure 1:
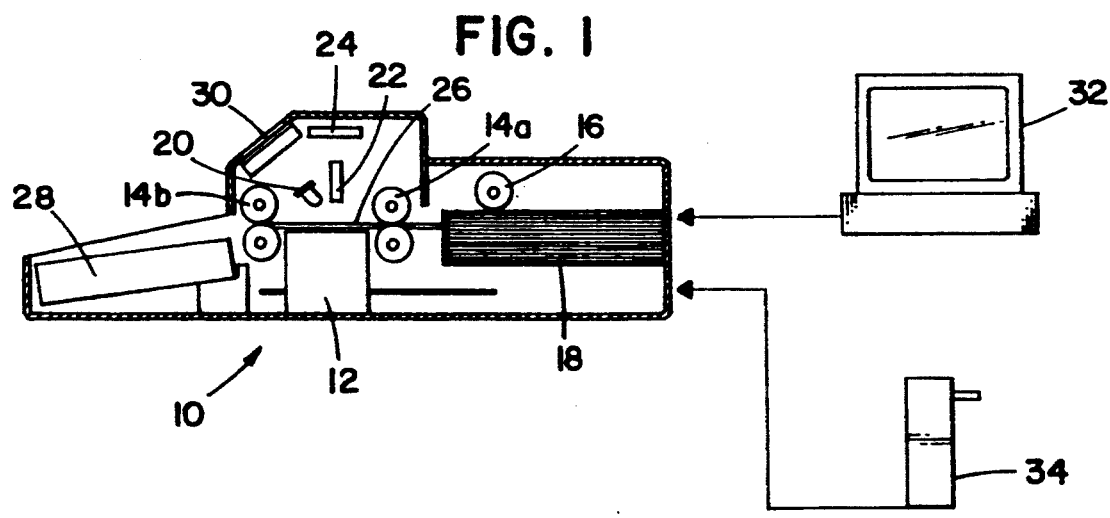
FIG. 1 is a cross-sectional side view of the present invention, illustrating the relationship between the components of the preferred embodiment.

FIG. 1 depicts the preferred apparatus of the present invention in a cross-sectional view for clarity. This preferred apparatus of the present invention is designed for counting the number of microorganism colonies on disposable culturing devices such as PETRIFILM TM (see FIG. 2), although objects on any substrate could be counted using appropriate modifications to the hardware and control systems. One example of another application is the inspection of moving webs for defects that occur as distinct objects.

Figure 2:
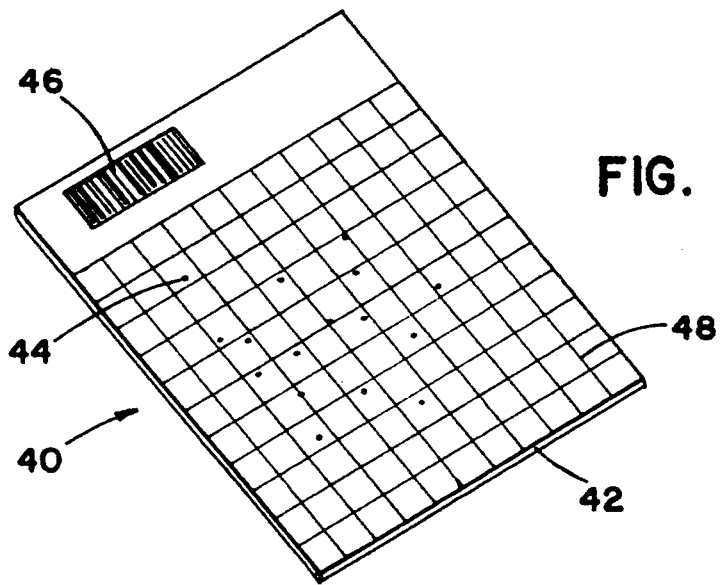
FIG. 2 is a top perspective view of a disposable microorganism culturing device such as PETRIFILM TM having a number of colonies located thereon.

FIG. 2 depicts a disposable microorganism culturing device 40, such as the PETRIFILM TM product described above. The device includes a substrate 42 having microorganism colonies 44 located on its surface. In a preferred embodiment, the substrate 40 also preferably includes a barcode 46 at its upper edge for identifying individual samples. The barcode is particularly useful for tracking storage and transfer of data. PETRIFILM TM products also typically include a series of grid lines 48 which are useful for manual counting of colonies. Although the preferred apparatus is designed for use with PETRIFILM TM products, it will be understood that any similar product having a substantially planar substrate with nutrients adhered to its surface for the culturing of microorganisms could be used in place of PETRIFILM TM products.

FIG. 1 depicts a preferred embodiment of the present invention. The counter 10 includes a motor 12 which is preferably a DC stepping motor. Motor 12 is operably connected to rollers 14a, 14b and 16 to move a substrate 26 through counter 10 for scanning. The substrate 26 enters the counter 10 on the right and moves through to the left end of the apparatus. A stepping motor is used to provide accurate incremental movement of the substrate 26 through the counter 10.

The preferred counter 10 includes a linear LED array 20 aimed at the substrate 26. The preferred LED array is Model No. TLG6A13P manufactured by Toshiba Corporation. This LED array is particularly useful because it produces light in wavelengths that neutralize the grid array 48 present on one version of the PETRIFILM TM product (see FIG. 2). That grid array is yellow to the naked eye. A similar effect could be duplicated with light sources producing other wavelengths by using a reddish-yellow filter (Wratten filter #9 or Corion LL-550-S-4385) between the CCD sensor 24 and light source.

The preferred LED array 20 is also useful for the present application because the intensity of the light produced across the array is substantially uniform which aids in the accuracy of the apparatus.

Located above substrate 26 in the preferred counter is linear array of SELFOC lenses 22, Model No. SLA-12-TC43A6, manufactured by Nippon Sheet Glass Co. This rod lens array 22 is widely used in facsimile machines as well as some photocopying equipment. Above the SELFOC lens array is a linear CCD sensor array 24, preferably Model No. TCD127AC, manufactured by Toshiba Corporation.

Figure 3:
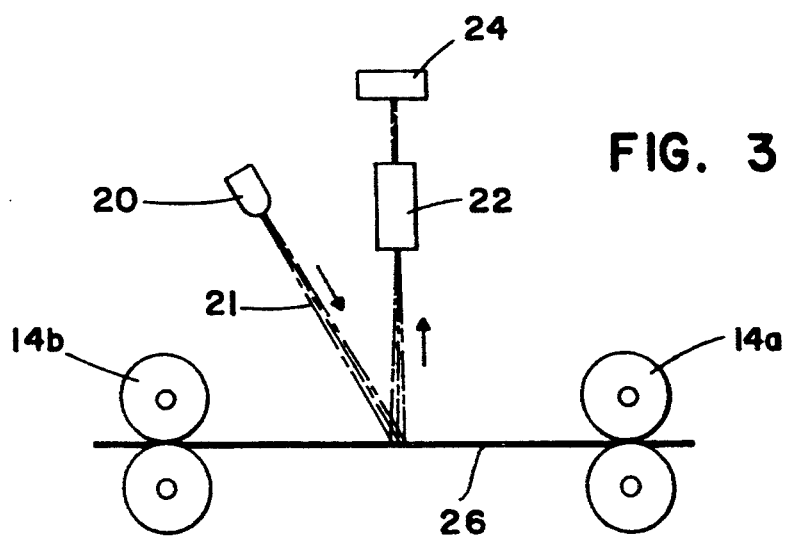
FIG. 3 is an enlarged cross-sectional side view of the scanning area of the preferred apparatus.

FIG. 3 is an enlarged view of the scanning area of the preferred apparatus. As shown there, LED array 20 produces light 21 which reflects off of substrate 26 and is at least partially reflected through the SELFOC lens 22 which focuses the light on the CCD image sensor 24. Rollers 14a and 14b are used move the substrate 26 through the scanning area. As discussed above, the rollers are preferably connected to stepping motor 12 for accurate incremental movement of the substrate 26 through the scanning area.

Also depicted in FIG. 1, the input end of the counter 10 is adapted to receive a cassette 18 which holds a stack of substrates 26 for automatic feeding through the counter 10. Roller 16 is placed above the cassette mechanism 18 and rests on the topmost substrate 26 to automatically feed it into the counter 10.

Figure 4:
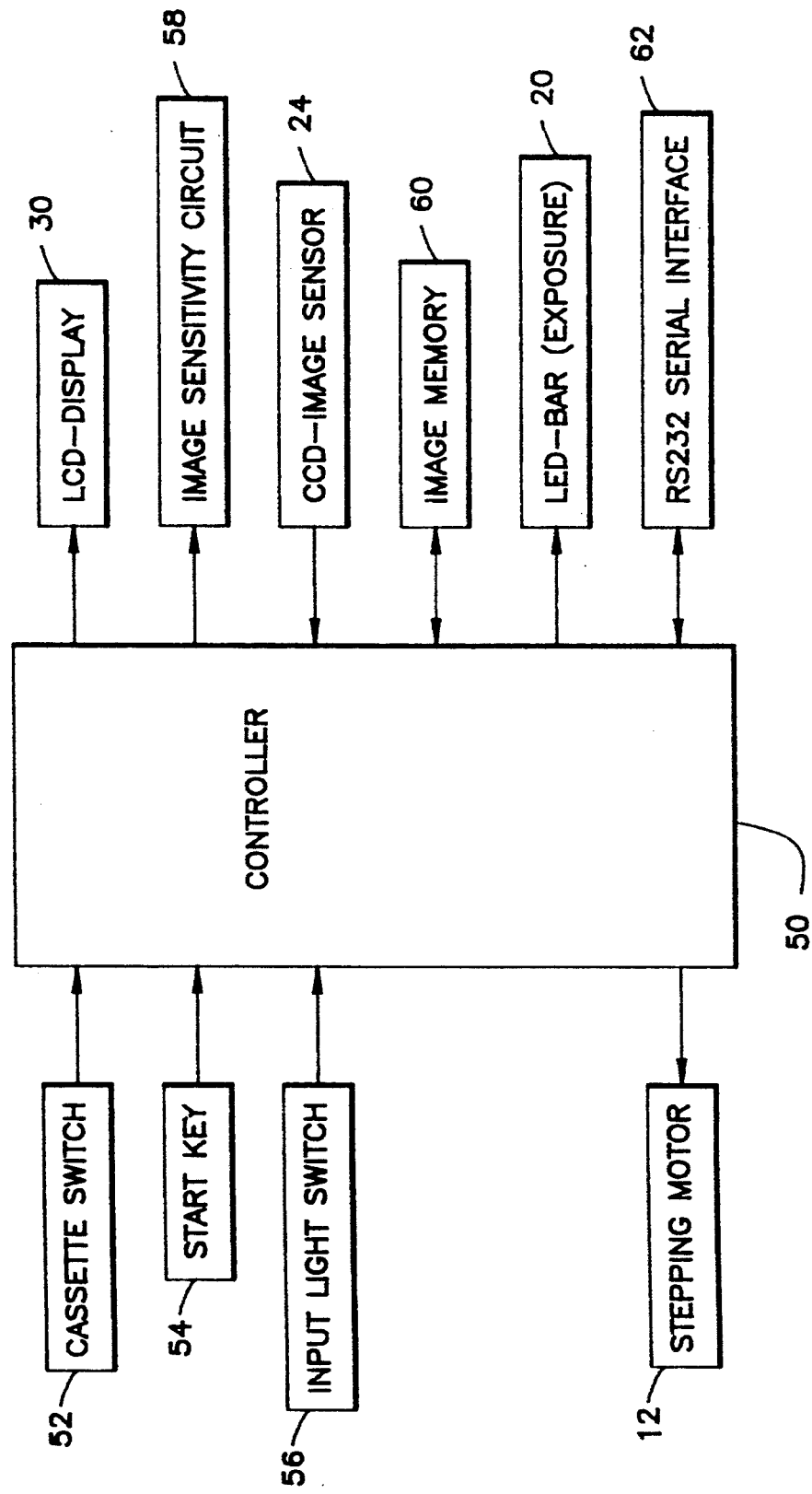
FIG. 4 is a block diagram illustrating the control system of the present invention.

FIG. 4 is a block diagram illustrating the preferred control system of the present invention. As illustrated, the CCD image sensor 24 is connected to the microprocessor 50. The preferred microprocessor 50 is an 8-Bit CMOS Microcontroller, Model No. 80C535, manufactured by Siemens AG.

Data from the CCD image sensor 24 is stored in the image memory 60 also connected to the microprocessor 50. In the preferred embodiment, this data is produced in a raster-scanned format for use with the preferred algorithm as discussed in more detail below.

The LCD display 30 is used to provide messages to the operator and prompt actions by the same. The cassette switch 52 is used to indicate whether a cassette 18 (see FIG. 1) is loaded in the counter 10. The start key 54 is used to begin the process of moving a substrate 26 into the scanning area and performing the scanning process. The input light switch 56 is used to indicate whether a substrate 26 has been moved into the scanning area.

The stepping motor 12 is used to incrementally advance substrates 26 through the scanning area and out of the counter and is operably connected to the rollers 14a, 14b and 16 shown in FIGS. 1 & 3. The rollers are preferably gear-driven, although any suitably accurate connection method can be used.

The LED bar array 20 is used to illuminate the surface of the substrate 26 and any objects on it for sensing by the CCD image sensor 24. The CCD image sensor 24 is used to detect objects from the reflected light. The image sensitivity circuit 58 is used to adjust sensitivity of the CCD image sensor 24 to a level below which a blank substrate 26 will not trigger the image sensor. An advantage of this circuit is that it automatically adapts to variations in the background presented by different substrates.

The image memory 60 is used to store data from the CCD image sensor 24 and is used to detect the number of distinct objects on the surface of the substrate 26 using the preferred algorithm described below. The RS-232 serial interface 62 is used to provide communication between the present invention and a computer or other electronic device. As shown in FIG. 1, the counter 10 is preferably connected to a computer 32 via the RS-232 interface to allow transfer of data between the computer and the counter 10.

Figure 5:
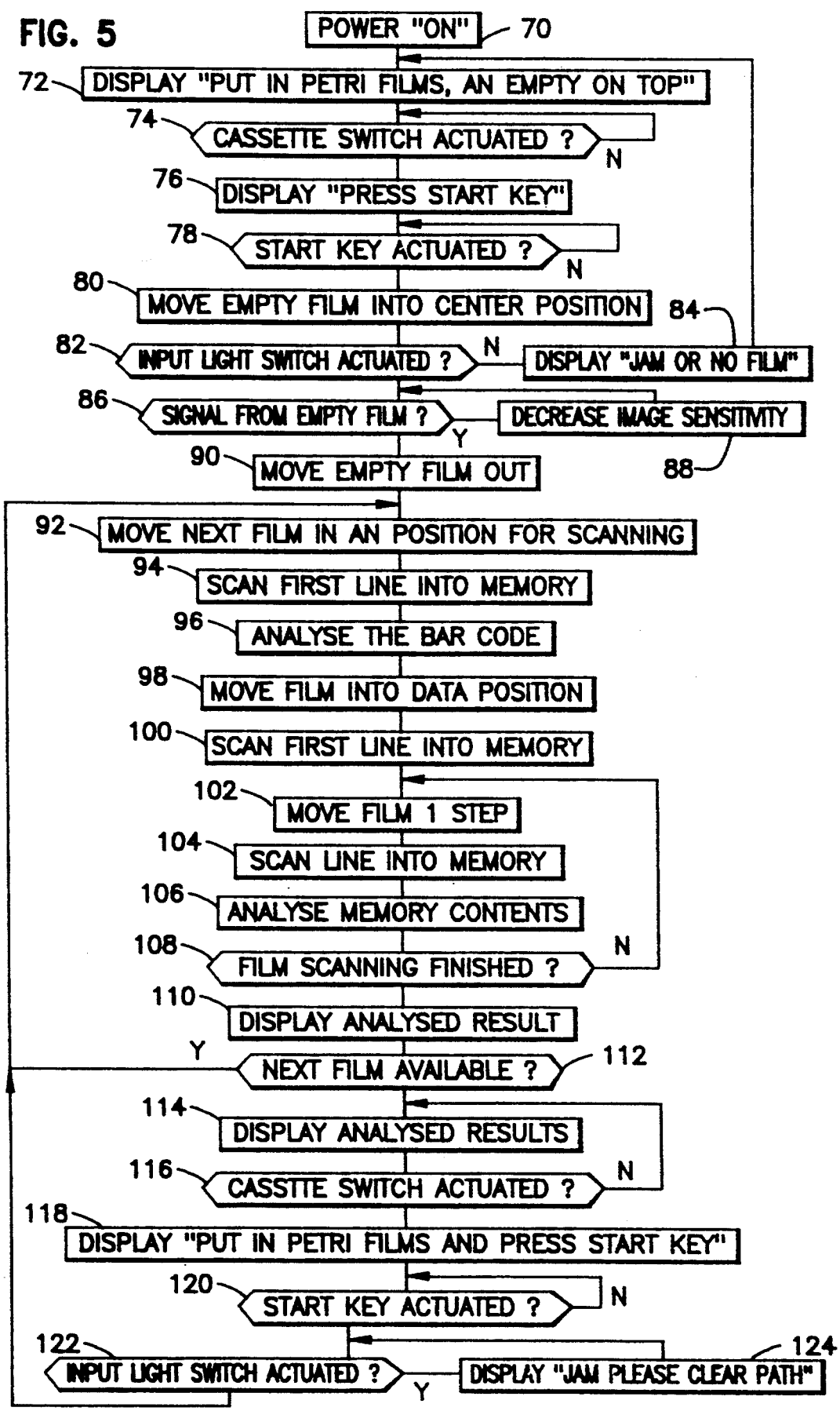
FIG. 5 is a flow chart depicting operation of a preferred embodiment of the present invention.

FIG. 5 is a flowchart showing operation of the preferred embodiment of the present invention which includes a cassette to automatically feed substrates into the counter 10. It will be understood by those skilled in the art that features of this flowchart would not be applicable to a counter designed to scan individually-fed substrates.

To begin the process, the counter 10 is powered up 70 and the LCD display indicates that a cassette containing a number of substrates should be loaded into the counter with a blank (empty) substrate placed on top 72. The blank substrate is used to adjust the sensitivity of the CCD image sensors in order to avoid errors in the detection process. Once cassette is loaded, the LCD display reads "Press Start Key" 76.

After Start Key is activated, the empty substrate is moved into the center of the counter 80, also referred to above as the scanning area. The counter also preferably includes an input light switch which indicates that a substrate has actually been moved into the scanning area 82. If no substrate (or film) is present the LCD display would read "Jam" or "No Film" 84 to indicate to the operator that an error in operation had occurred.

Once an empty substrate is in position the scanning process begins. If the blank substrate generates a signal from the CCD image sensor 86, the image sensitivity circuit automatically decreases sensitivity of the CCD image sensor 88 to a point at which no signal is generated from the empty substrate.

After the CCD image sensor sensitivity is set, the empty substrate is moved out of the counter 90 and the first substrate with microorganism colonies is moved into position for scanning 92. The first line would then be scanned into memory 94 and if that line included a barcode, the barcode would be placed into memory indicating the identity of the sample located on the substrate 96.

The substrate is then moved into the scanning area (data position) 98 and the first line of data is scanned into the image memory 100. The substrate (film) is moved one step by the stepper motor 102 and the next line is scanned into memory 104. The memory contents are then analyzed 106 according to the preferred algorithm described below. Scanning continues in this stepwise fashion until the entire substrate is scanned 108.

After the scanning is finished, the results of the scanning process are displayed 114 and could be transferred to a computer or other electronic device using the RS-232 serial interface which is a part of the preferred embodiment of the present invention. The controller determines if an additional substrate is available in the cassette 116 and, if so, the above process is repeated. After all the substrates in the cassette have been scanned, the counter 10 signals that the process is complete.

Although the preferred apparatus as described above includes an LED array producing light with a peak wavelength of 567 nm, it will be understood that many other types or methods of detection other than those discussed above are also possible. In particular, the present invention could use light sources that are fluorescent or the CCD image sensors could be used to detect chemiluminescent colonies. In addition, the detectors could be sensitive to specific colors or could detect radiation emanating from colonies.

Also, although the preferred embodiment of the apparatus includes the hardware described above, alternate embodiments can be developed using other hardware. Because the data from the line scanners is in raster-scanned format, a simple line delay device (e.g., several FIFO's strung together or static RAM with independent read/write address hardware) will provide access to two lines of the raster-scanned image. A shift register and a bank of comparators can then determine the bit pattern triggering the object start and object merge conditions described in more detail below. Alternatively, a shift register output can be directly used as the address of data into a lookup table. Summing hardware could then count the number of object start and object merge conditions detected by either the lookup table or by the comparators.

PREFERRED OBJECT COUNTING ALGORITHM

Figure 7:
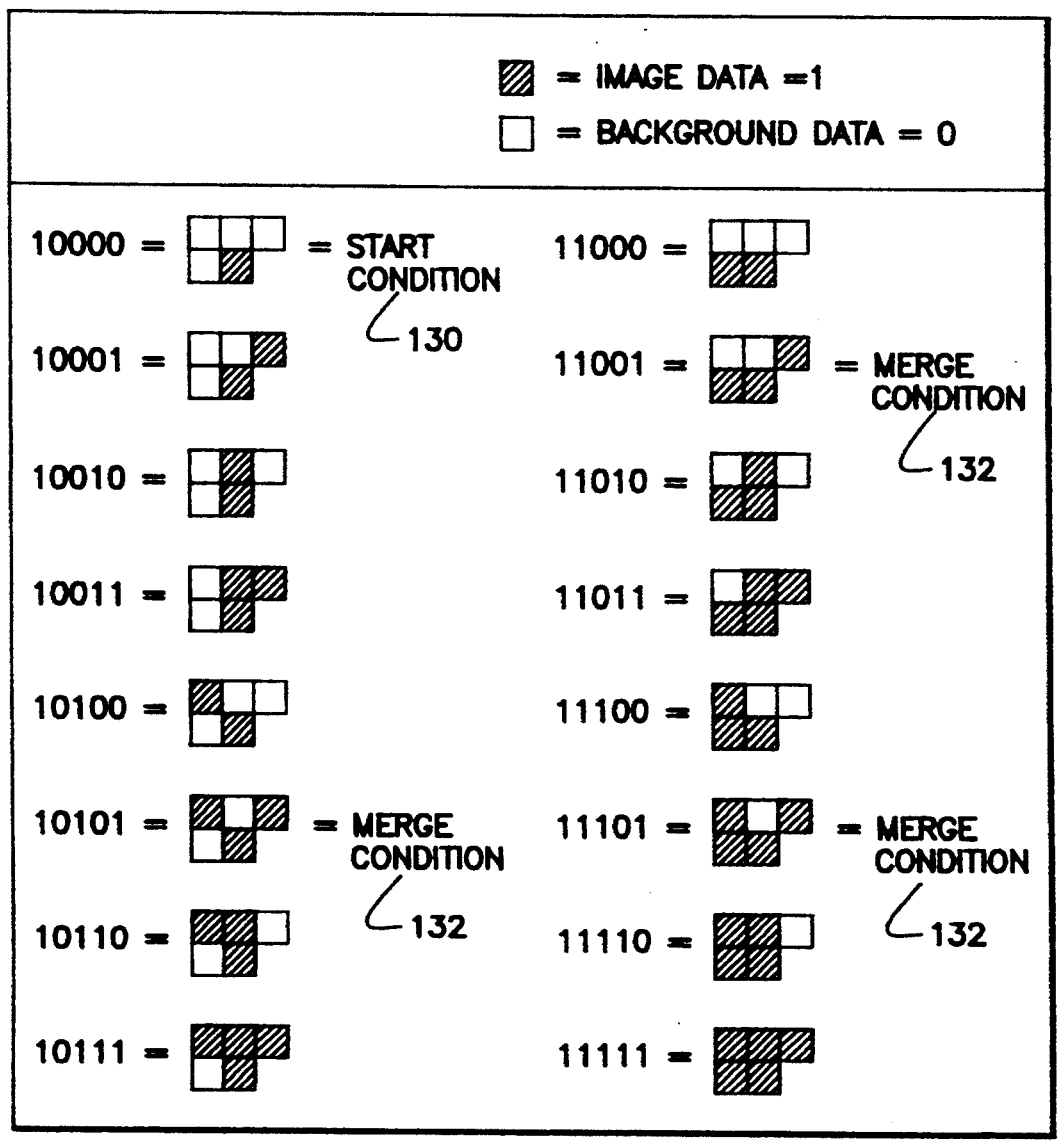
FIG. 7 is a table illustrating the 16 possible pixel regions used in processing image data in the preferred algorithm of the present invention.
Figure 8:
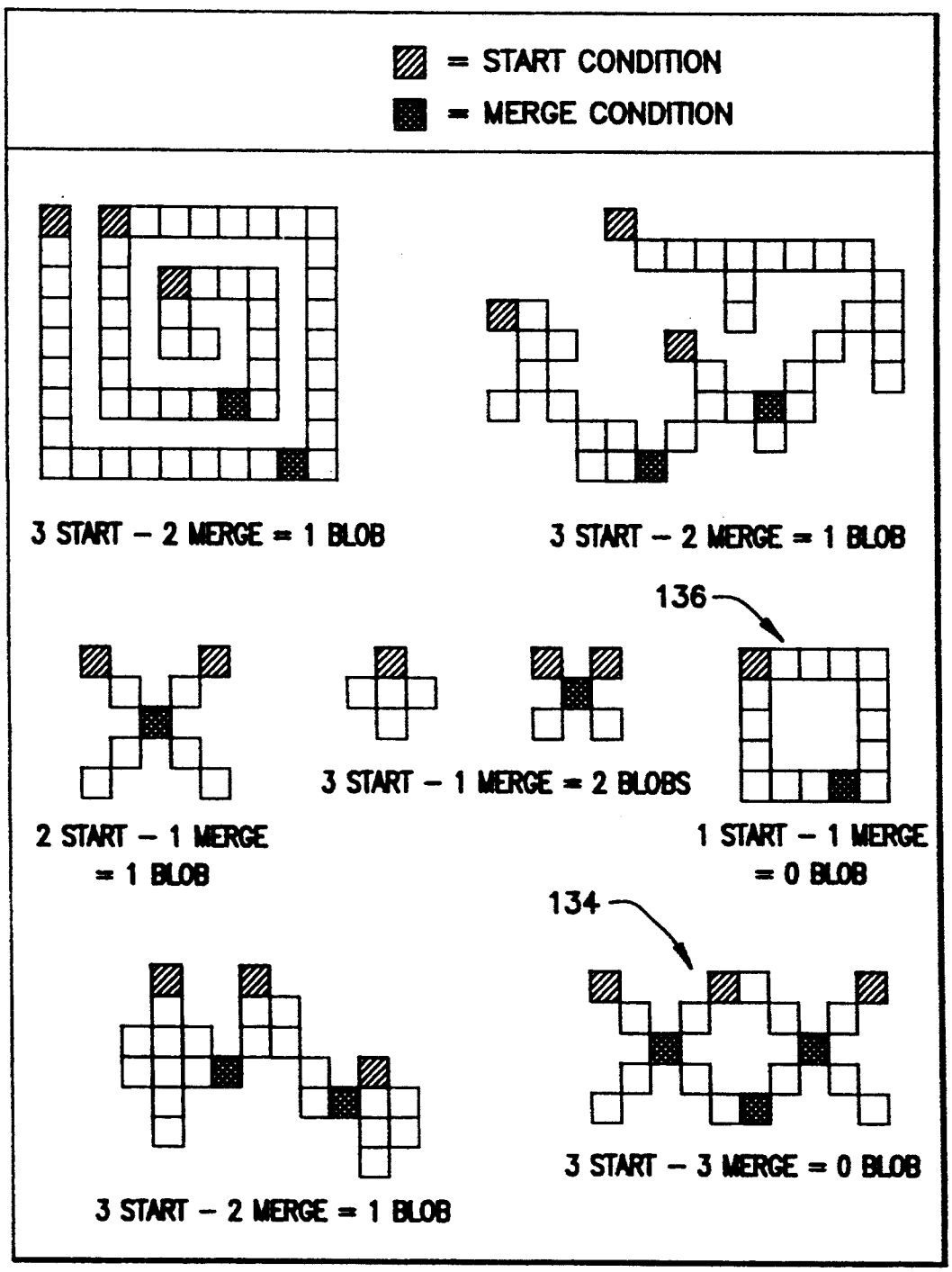
FIG. 8 is a table of examples of possible objects encountered by the present algorithm and the outcome of the preferred algorithm after processing these objects.

The preferred algorithm for counting the number of distinct objects in the scanned area of the substrate is described below, with reference to FIGS. 6-8. In essence, the algorithm searches the data stream to detect object starts and object merges. The total number of distinct objects in a scanned image is equal to the number of object starts minus the number of object merges.

It will be understood by those skilled in the art that many other algorithms could be used to scan objects such as substrates having microorganism colonies located on them. Examples of algorithms include the SRI (Stanford Research Institute) algorithm or an Euler number analysis. The present invention is, however, most advantageously used with the preferred algorithm described below.

The preferred algorithm is designed for use with a raster-scanned data format to provide high speed inspection capabilities. That format treats the image as a two-dimensional array of data which may only be accessed along successive rows in a left-to-right manner. As a result, it is difficult to access more than a small portion of the image at any single time. The pixel of interest passes through the image in a raster scanned manner and, thus, the portion of the image available for processing must also pass through the image with the pixel of interest.

Figure 6:
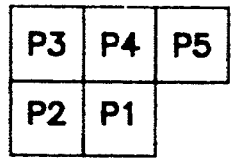
FIG. 6 is a diagram of the pixel region used in the preferred algorithm of the present invention.

The preferred algorithm uses the sigma-shaped neighborhood depicted in FIG. 6 for image processing. The addition of the fifth pixel (P3) to the standard 2×2 processing neighborhood allows for 8-connected object analysis not available with a Euler number analysis. Also, because any given pixel is either part of an object or part of the background, grey level images are preferably converted to binary format where the object is white (pixel value=1) and the background is black (pixel value=0). That conversion is accomplished before the data is processed with the preferred algorithm.

In use, the algorithm passes the sigma region across the image in a raster-scanned Order so that pixel P1, the pixel of interest, is centered on each pixel in the image exactly once (appropriate delay lines may be necessary if pipeline operation is desired).

With only five pixels in the sigma region there are only 32 possible combinations of image data in a binary system. Of the 32 combinations, only those in which P1=1 are part of an object. If pixel P1=0, then it is part of the background and is not applicable for counting. Only 16 of the possible 32 combinations satisfy the above condition. These 16 combinations are depicted in FIG. 7.

In this group of patterns, only four are used in the preferred algorithm. They break down further into a "Start Condition" 130 and three "Merge Conditions" 132, as depicted in FIG. 7. The Start Condition 130 has a binary value of 10000, while the three Merge Conditions 132 have values of 10101, 11001 & 11101.

The preferred algorithm is based on the principle that any object in the scanned image must have a starting place. That condition is most easily seen with the Start Condition 130 which represents the first pixel of an object as viewed in the raster-scanned data format. Problems arise, however, because a single distinct object may have several pixels whose neighborhoods match the starting case. A tree-like object may have multiple branches, each with unique pixels matching the Start Condition and which eventually "merge" into a single object.

The preferred algorithm relies on the three unique Merge Conditions to prevent multiple counting of a single distinct object. The Merge Conditions occur when seemingly distinct objects combine to form a single distinct object. Those Merge Conditions 132 are illustrated in FIG. 7.

In the counting process, the data stream is searched to detect an object start (Start Condition) whenever P1=1 and P2–P5 all equal 0 (rendering the binary data stream 10000) and an object is added to the object sum. Likewise, the data stream is also searched for any of the three object merges (Merge Conditions). When an object merge is detected, an object is subtracted from the object sum. Thus, the final object sum is the sum of all the object starts found less all of the object merges.

Because of the small sigma-shaped processing neighborhood and the use of object merges to adjust for multiple counting, the preferred algorithm is global in nature, i.e., a final object sum is not available until the entire image is scanned and processed.

It should be noted that the preferred algorithm is not perfect. Complex shapes can be miscounted with the final object sum tending to be lower than the actual number of distinct objects found in the image. Referring to FIG. 8, examples of some possible complex shapes is illustrated along with an analysis of how the preferred algorithm would count these shapes. In particular, the preferred algorithm will typically fail to count objects having holes in them, two of which are illustrated as objects 134 and 136.

In spite of this failing, the preferred apparatus and algorithm provide colony counts that are well within the allowed margin of error as compared to manual counting. In addition, the preferred method of use includes manual screening of the substrates prior to automated counting to remove those substrates in which the colonies have merged to form a global colony which would likely be miscounted by the present invention.

That failure exists because, for any given merge condition, the algorithm cannot discern whether the two branches surrounding the hole are distinct or if they had split from a single object farther above in the image. This problem cannot be remedied without a complicated and expensive global object labeling feature which defeats many of the advantages accompanying the preferred algorithm and apparatus. In spite of this drawback, the present algorithm does count the vast majority of objects with sufficient accuracy to be very useful in many image processing tasks.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

We claim the following:

1. A method of counting microbial colonies growing in a solid media on a substantially planar substrate culture device comprising the steps of
   a) incrementally scanning substantially straight lines across the planar substrate culture device to generate a first line pixel data and a second line pixel data corresponding to detected colonies;
   b) storing the first line pixel data and at least two pixels from the second line pixel data;
   c) comparing portions of the stored first line pixel data and second line pixel data to record object starts or object merges; wherein the portion of the second line pixel data consists of P1, a present pixel and P2, a previous, adjacent pixel from the second line pixel data and the portion of the first line pixel data consists of P4, a pixel from the first line pixel data in the same position as P1; P3, an adjacent pixel recorded before P4; and P5, an adjacent pixel recorded after P4;
   d) recording an object start when the pixel value for P1 is 1 and the pixel values for P2, P3, P4, P5 are 0; or
   e) recording an object merge when
      i) when the pixel values for P1, P3, P5 are 1 and the pixel values for P2 and P4 are 0; or
      ii) when the pixel values for P1, P2 and P5 are 1 and the pixel values for P3 and P4 are 0; or
      iii) when the pixel values for P1, P2, P3, and P5 are 1 and the pixel value for P4 is 0;
   f) changing the position of the planar substrate culture device to scan incremental lines of the planar substrate, wherein the number of colonies growing in the solid media is a total of recorded object starts minus recorded object merges.

2. A microbial colony counting apparatus comprising
   a) a linear array of light sensitive detectors intersecting a substantially planar substrate culture device containing microbial colonies growing in a solid media, wherein the detectors intersect the planar substrate in a substantially straight line and measure pixel values in the linear array, wherein pixels values on a white side of predetermined threshold are recorded as a value of 0 and pixel values on a black side of the threshold are recorded as a value of 1,
   b) processing means to record and manipulate the pixel values measured by the detectors,
   c) indexing means for incrementally changing the position of the planar substrate relative to the detectors to provide more than one indexed position of the planar substrate wherein the change of position is substantially perpendicular to the, substantially straight line intersection of the linear array with the planar substrate,
   d) colony counting means for determining the number of colonies growing in the solid media on the planar substrate wherein three pixel values recorded from a first indexed position of the planar substrate are compared to two pixel values from an adjacent, second indexed position, wherein the pixels from the second indexed position consist of P1, a present pixel on the second linear array and P2, a previous, adjacent pixel on the second linear array, and the pixels from the first indexed position consist of P4, a pixel from the same position as P1 in the first indexed position, P3, an adjacent pixel recorded before P4, and P5, an adjacent pixel recorded after P4, wherein an object start is recorded when the pixel value for P1 is 1 and the pixel values for P2, P3, P4, P5 are 0; or wherein an object merge is recorded when
      i) the pixel values for P1, P3, P5 are 1 and the pixel values for P2 and are 0; or
      ii) the pixel values for P1, P2 and P5 are 1 and the pixel values for P3 and P4 are 0; or
      iii) the pixel values for P1, P2, P3, and P5 are 1 and the pixel value for P4 is 0; wherein the number of colonies growing in the solid media is a total of recorded object starts minus recorded object merges.

3. The apparatus of claim 2, wherein the linear array of light sensitive detectors comprise a CCD sensor array.

4. The apparatus of claim 2, further comprising a light source positioned to produce light striking an upper surface of the substantially planar substrate and which is capable of providing light having a substantially uniform intensity across the substantially straight line intersection at the linear array with the planar substrate.

5. The apparatus of claim 4, wherein the light source is a linear LED array.

6. The apparatus of claim 2, further comprising focusing means for focusing light reflected from an upper surface of the substantially planar substrate to the detectors.

7. The apparatus of claim 6, wherein the focusing means comprise a linear array of lenses.

8. The apparatus of claim 7, wherein the linear array of lenses comprise a linear array of SELFOC lenses.

9. The apparatus of claim 2, wherein the indexing means comprise an incremental stepper motor operatively connected to at least one roller for changing the position of the planar substrate.

* * * * *

UNITED STATES PATENT AND TRADEMARK OFFICE
CERTIFICATE OF CORRECTION

PATENT NO. : 5,403,722
DATED : April 4, 1995
INVENTOR(S) : Steven P. Floeder, Josef A. Graessle, John C. Schultz, Werner R. Schwarz and Frederick M. Waltz It is certified that error appears in the above-indentified patent and that said Letters Patent is hereby corrected as shown below:

Col. 3, line 61     "witch" should read --with--

Col. 5, line 22     after "used" please insert --to--

Col. 6, line 24     after "Once" please insert --the--

Col. 7, line 65     "Order" should read --order--

Signed and Sealed this

Fourteenth Day of November, 1995

Attest:

BRUCE LEHMAN

Attesting Officer     Commissioner of Patents and Trademarks